United States Patent [19]

Thorell

[11] 4,394,391

[45] Jul. 19, 1983

[54] RADIOIMMUNOASSAY REAGENTS

[76] Inventor: Jan I. Thorell, Beleshogsvagen 1, S-21618 Malmo, Sweden

[21] Appl. No.: 122,212

[22] Filed: Feb. 19, 1980

[51] Int. Cl.³ .................. A61K 45/00; A61K 47/00; A01N 25/10
[52] U.S. Cl. ..................................... 424/366; 23/920; 252/408.1; 422/71; 424/1; 424/22; 424/358; 427/213.33
[58] Field of Search ................. 252/316, 408; 424/12, 424/22, 1, 366; 422/71; 23/920; 435/181

[56] References Cited

U.S. PATENT DOCUMENTS

| | | | |
|---|---|---|---|
| Re. 29,474 | 11/1977 | Axen et al. ........................ | 424/1 |
| 3,451,777 | 6/1969 | Di Giulio .......................... | 23/230.3 |
| 3,615,222 | 10/1971 | Mead ................................. | 422/71 X |
| 3,836,433 | 9/1974 | Wirth et al. ...................... | 424/12 X |
| 3,839,153 | 10/1974 | Schuurs et al. .................. | 424/12 X |
| 3,883,738 | 5/1975 | Glover et al. .................... | 250/303 |
| 3,905,767 | 9/1975 | Morris et al. .................... | 424/12 X |
| 3,966,897 | 6/1976 | Renn et al. ....................... | 424/12 X |
| 3,979,184 | 9/1976 | Giaever ............................. | 424/12 X |
| 4,000,252 | 12/1976 | Kosak ................................ | 422/71 X |
| 4,115,535 | 9/1978 | Giaever ............................. | 424/12 X |
| 4,158,135 | 6/1979 | Thorell .............................. | 250/303 |

FOREIGN PATENT DOCUMENTS 1529181 8/1977 United Kingdom .

OTHER PUBLICATIONS

Anal. Chem. 49, 1183A–1190A, (1977).
Nature 268, 437–438, (1977).
Chem. Abstr. 85, (1976), 173968e.

Primary Examiner—Richard D. Lovering
Attorney, Agent, or Firm—Fred Philpitt

[57] ABSTRACT

Attenuator compositions useful as reagents in an improved internal sample attenuator counting method for radioimmunoassays are described. These compositions comprise an attenuator material that have a high capacity to absorb emitted radiation from a radioligand of the radioimmunoassay and are combined with an immunologically reactive material which interacts with components of the radioimmunoassay or combined with an absorbent of the free radiolabelled component to separate bound from free radioligand.

11 Claims, 2 Drawing Figures

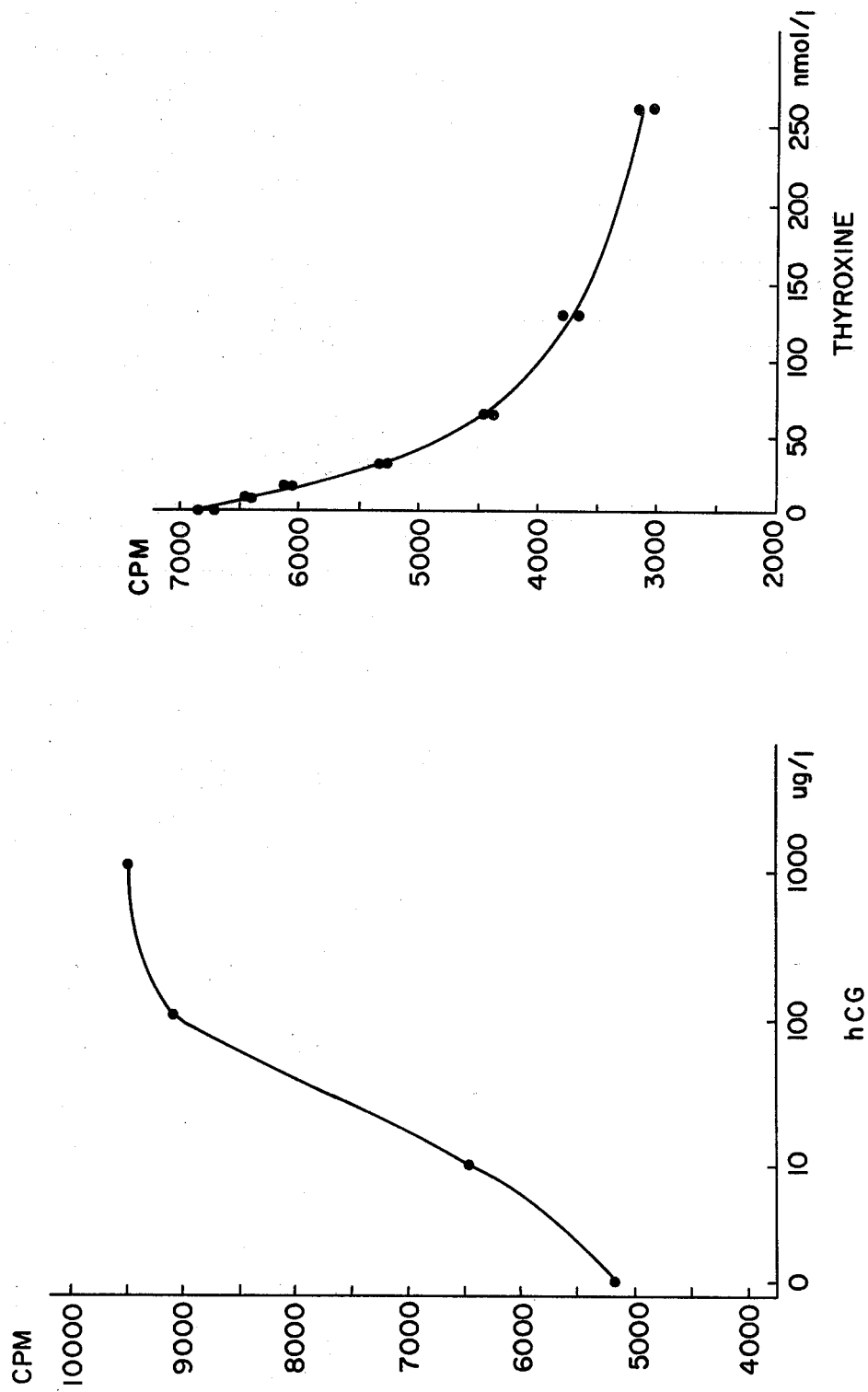

RADIOIMMUNOASSAY REAGENTS

BACKGROUND OF THE INVENTION

Radioimmunoassay and other radioligand assays involve a final separation step in which bound and free radioligand are separated into different phases to permit measurement of the radioactivity associated with one of the phases. In most assays the separation involves two procedures; first, a centrifugation, and then second, a removal of the soluble phase by decantation, suction or the like. Such procedures are work intensive and they are obstacles to the development of completely automated radioimmunoassay systems.

The removal of the supernatant leads to major difficulties of inprecision in the assay and a risk of contaminating the outside of the assay test tubes. An alternative approach which would obviate these difficulties is to separate the bound from free radioligand into different phases and then selectively shield the radiation from one of the phases while both phases are still within the assay test tube. The low energy gamma-radiation of $^{125}I$ (27—35 KeV), the dominating tracer of radioimmunoassays penetrates most high density materials quite poorly. By including an attenuating material in the assay, it is possible to prevent the radiation of one of the resulting phases from emerging from the tube.

U.S. Pat. No. 4,158,135 describes a method of analysis in which a radioactive substance is distributed in a liquid phase and a solid particulate phase, and radiation from one phase is measured while attenuating the radiation from the other phase by providing to the latter phase a radiation-absorbing material. In this manner the radioassay can be carried out without physically separating the two phases. The selection of suitable radiation absorbing materials depends in large part on the identity of the radioactive isotope used in the assay. Thus, for example, when the widely employed isotope $^{125}I$ is utilized, an effective attenuation of radiation is achieved with a wide variety of elements including those with a relatively low Z number. Suitable elements include silver, cadium, tungsten and bismuth. The specific embodiments described in the aforementioned patent use tungsten powder as the attenuating material.

In the selection of the proper attenuating material and its physical form, it is desired that such material does not interfere in the antigen-antibody binding or, if insoluble, does not adsorb the reactants of the assay onto its surface. Insolubilization of the bound or unbound radioligand to achieve separation of these components for measurements is achieved in the aforementioned patent by utilizing techniques and reagents known in the art, i.e., double antibody separation, chemical precipitation, or by utilizing antibodies or antigens bound to water insoluble polymers in particle form. Alternatively, the unreacted radioactive material is rendered insoluble by adsorbing it to a particulate adsorber, usually active charcoal which preferably is treated with dextran. The charcoal can be physically mixed with a radiation absorbing material to effect a further embodiment in the aforementioned patent. Finally, another alternative material utilized therein is a radioactivity absorber which also absorbs the unreacted radioactive material. An example of such material is bismuth carbonate powder.

BRIEF DESCRIPTION OF DRAWINGS

FIG. 1 is a graphic presentation showing the results of radioimmunoassays of human chorionic gonadotrophin at various concentrations demonstrating the effectiveness of the present invention in a standard curve.

FIG. 2 is a graphic presentation showing the results of radioimmunoassays for thyroxine at various concentrations demonstrating the effectiveness of the present invention in a standard curve.

DESCRIPTION OF THE INVENTION

The present invention relates to novel attenuator compositions useful as reagents in an improved internal sample attenuator counting method for radioimmunoassays and related radioligand assays. These compositions comprise individual particles each containing an attenuator material having a high capacity to absorb emitted radiation as a first active component and a material which will interact with a reagent or reaction product of the assay procedure as a second active component.

In one aspect of the compositions of the present invention, the second active component is selected from materials which are immunologically reactive with either the reagents or the reaction product of the radioimmunoassay. Thus, for example, suitable materials include antibodies (first antibody), specific to the substance to be assayed in the radioimmunoassay, antigens and antibodies (second antibody) raised in a second species against the sera of the host species in which the first antibody was elicited. The second active component may also be biologically active binders which are of non-immune types, such as transporting proteins like thyroxine binding globulin or receptors of cellular origin like cytoplasmatic estrogen receptors or hormone receptors from the plasma membrane.

The first active component can be any art recognized attenuator material having a high capacity to absorb radiation emitted by a radioligand. In particularly, such materials include those attenuator materials previously described for this purpose, i.e., silver, cadmium, tungsten, bismuth or compounds comprising such elements, such as the oxides thereof. A particularly preferred first active component comprises bismuth, particularly bismuth oxide ($Bi_2O_3$).

A preferred form of this aspect of the invention is obtained by providing the aforesaid first and second active components in conjunction with a support matrix. Such matrix can be obtained from gels, glass or polymeric materials which have been conventionally employed in the art to immobilize biologically active molecules. Preferred matrix materials for this purpose include agarose, polyacrylamide, starch or polyvinylidene-fluoride.

A convenient procedure for preparing a composition in accordance with this aspect of the invention is to insolubilize, gel or polymerize the matrix material in the presence of the first active component so as to obtain particles, preferably micro particles, of the polymeric material containing the first active component. The second active component is then covalently coupled to the surface of the particles, or covalently coupled to or entrapped by the matrix of the particles, utilizing procedures known in the art for coupling or entrapping or otherwise immobilizing biologically active substances onto the solid support material.

The size and properties of such particles depend to a large extent on the properties of the first active component. It is preferrable that this component is in a microcrystalline form with the largest crystal dimension below 5 microns. Larger particles are suitable, however the most preferred size is one with 2 micron crystal dimension. Thus, for example, a suitable first component such as bismuth oxide, can be incorporated into a polyacrylamide matrix by polymerizing the acrylamide monomer in the presence of the bismuth oxide. The polymerization is conveniently carried out in a water-organic solvent emulsion. Because of the high density of particles containing bismuth oxide it is desirable to carry out the polymerization using a high density organic solvent such as carbon tetrachloride as the organic phase. In an alternative procedure, an organic solvent of lower density such as toluene is used to allow the particles to sediment during polymerization.

The polymerization reaction mixture, in addition to the above components, will also contain a conventional polymerization inducing agent for the monomer employed and a conventional emulsifier such as Mannitan monooleate which is commercially available as Arlacel A from Serva, Heidelberg. A representative polymerization reaction mixture comprises the following components in parts by weight: 0.4 to 2.0, preferably 1.9 acrylamide; 0.2 to 0.4, preferably 0.4 N,N'-methylenebisacrylamide; 0.1 to 2.0, preferably 1.0 bismuth oxide; approximately 10.0 water; and an organic phase of 50 to 250 ml carbontetrachloride containing 1 to 4, preferably 2% Arlacel A. The polymerisation of polyacrylamide into a matrix is activated by 0.1 to a 50% ammonium persulphate in water and 0.4–0.5 $N,N,N^1, N^1$-tetramethylethylene diamine and carried out at a temperature in the range of from about 0° to 10° C., preferably at about 2° C.

Other than polyacrylamide, choices of matrices include agarose 1–5%, preferably 2%, or starch 40–80%, preferably 60%. The matrix, (agarose or starch) in heated and melted form is mixed with the first active component into a homogenous suspension. As with polyacrylamide, the aforementioned suspension is gelled into particles in a water-organic solvent system. Droplets of the starch or agarose gel product or the polyacrylamide polymer are then caused to solidify to solid particles of the desired size ranging from 1 to 100 microns, preferably less than 10 microns. These particles will have a density ranging between 1.2 and 8.0 grams per cubic centimeter. To obtain a separation of the particles during their solidification, the organic solvent phase may be agitated, as by stirring, or sonicated.

Another choice of matrix is polyvinylidenefluoride (PVF). A range of 0.4–3.0 grams, preferably 2.0 grams of PVF dissolved in 20 ml of dimethylformamide is mixed with 10–50 grams, preferably 40 grams, of bismuth oxide. Droplets of the resulting material is caused to solidify into small particles of the desired size, ranging from 1 to 100 microns, by mixing said material into 200 to 500 ml of isopropanol, ethanol, or water. The size of the particles may be further reduced by homogenization.

In an alternative embodiment of this aspect of the invention, the first and second active components can be intimately co-mixed with the gel or polymeric material in molten, dissolved or non-polymerized form which mixture can then be casted or otherwise insolubilized into a rigid matrix which is then finally divided, such as by grinding, to the desired particle size range. Alternatively the matrix is first coarsely divided, suspended into a waterphase and then homogenized with a homogenizer (e.g. Polytron) to the desired particle size.

Independent of the method used to produce the particles, it may be desired to achieve a more narrow range of particle sizes then produced with this method. In this case, the particles produced may be separated according to size by sieving, or by sedimentation in a fluid or in a stream of air.

To obtain the desired sedimentation characteristics of the various types of particles, the suspension in which they are contained may also include surface active components like Tween-20, dextran, polyethyleneglycol or proteins in concentrations well known to affect the aggregation of particles in suspension.

Coupling of the second active component to the resulting particles containing active first component dispersed within the gel or polymeric matrix can be accomplished by utilizing bonding agents such as cyanogen bromide or a bivalent coupling agent, such as a dialdehyde, preferably glutaraldehyde which acts as a linking group between reactive groups in the surface of the matrix and reactive groups of the second active component.

When PVF is used as a matrix, coupling of the second active component in the form of an antiserum may be achieved by treatment of PVF coated bismuth oxide particles with isopropanol for 1 hour after which the particles are washed 3 times with 0.1 M phosphate buffer pH 7.0 containing 0.15 mol sodium chloride. Then the particles are incubated for 24 hours at room temperature.

In one embodiment of this invention the sedimentation rate, obtained by employing conventional sedimentation procedures, of the particles containing the first and the second active component is selected to match the reaction rate of the second active component. By selecting a combination of particle size and particle density within the ranges mentioned above the sedimentation rate of the particles may be specified so that they will settle at bottom of the tube within a certain time period, ranging from 1–180 minutes preferably 15–30 minutes. The binding capacity of the second component of the particles is so high that the immunological reaction desired will take place during the sedimentation of the particles. In an alternative form of this embodiment, the first component of the particles are substituted by a material with the same high density as those mentioned in the foregoing, but with a much less radiation absorbing capacity. Suitable radioactive isotopes include the radioactive forms of barium and iodine containing compounds. When the particles have sedimented to the bottom of the test tube, the supernatant has to be removed from test tube to permit the measurement of its contents of radioactivity or alternatively to permit the measurement of the radioactivity associated with the sediment.

In a special form of this invention, the particles containing the first and second active components are divided into separate dosing units in dried or lyophilized form. Each dosing unit is pressed into a tablet form. The tablet also contains filling media needed to maintain the tablet form and to accelerate its disintegration when suspended in water. Such tablet compositions are well known in the pharmaceutical industry and include filling media such as starch, lactose or magnesium carbonate. In this form, the precise addition of a predetermined amount of the active components to each test tube is improved and facilitated.

In a specific embodiment of this aspect of the invention a goat anti-rabbit second antibody was coupled to particles containing bismuth oxide dispersed within polyacrylamide, said particles prepared by utilizing glutaraldehyde as described above. The resulting material was used in a radioimmunoassay of human chorionic gonadotrophin, (HCG) using solid phase-attenuator double antibody separation. In this assay HCG standards (0.1 ml) $^{125}$I-HLH (0.2 ng) and rabbit antiserum against HCG (1:4,000) in a total volume of 0.5 ml were incubated for 1 hour at room temperature. Then, 1 ml of a suspension containing 0.1 ml of second antibody-bismuth oxide-polyacrylamide particles and 0.4 g. bismuth oxide suspended in 1 ml of buffer were added. The tubes were rotated slowly for 3 hours. Then they were left standing for 15 minutes to sediment and then counted in a well counter. The resulting data is summarized in the standard curve shown in FIG. 1 of the accompanying Drawings.

In an alternative embodiment, rabbit antibody to HCG was coupled to bismuth oxide containing polyacrylamide particles. A constant amount of such particles was incubated with HCG standards and $^{125}$I-HLH in a total incubation volume of 1 ml. The tubes were rotated slowly over night. Then they were left standing for 15 minutes to permit the particles to sediment. They were counted in a well counter. The results were essentially identical with those illustrated in FIG. 1.

In a second embodiment of the second active component there is employed material which interacts with the radioligand component of the radioimmunoassay reaction mixture by adsorption. In this embodiment charcoal is the preferred second active component. Suitable compositions containing charcoal and the first active component are readily obtained by mixing these components in conjunction with a binding agent (solid support matrix) such as agarose and then forming the composition into the desired particles. By producing and/or selecting particles of a desired size and density, their sedimentation rate is chosen to give an optimal adsorption of the radioligand component. In a specific embodiment bismuth oxide was coated with charcoal using agarose as binder (solid support matrix) according to the following procedure. One hundred grams (100 g) of bismuth oxide was mixed with 1.0 to 100 g preferably 2.5 g of active charcoal. A total of 25 ml of melted 1.5% agarose was added and the mixture was stirred until homogeneous. It was left in a refrigerator over night. The gel was carefully ground with a mortar. The fragmented gel was suspended in 250 ml of 0.075 M barbital buffer containing 0.25% bovine serum albumin and 0.05% Dextran T70. Alternatively other matrix materials mentioned previously, like starch, polyacrylamide and PVF may be used with charcoal, the second active component. The charcoal is mixed with the bismuth oxide in the proportions given above, after which particles of the matrices are produced as described when the particles contained the matrix material and bismuth oxide only.

1 ml of this suspension was used as absorber-attenuator in a radioimmunoassay for thyroxine (T$_4$). In such assay 0.05 ml of T$_4$-standards were incubated with 0.2 ml of rabbit antiserum to T$_4$ (1:100) and 0.2 ml of $^{125}$I-T$_4$ (200 pg) at 4° C. overnight. A suspension of 0.4 g of charcoal bismuth oxide-agarose particles in 1 ml of buffer was added. The tubes were vortexed for 5 seconds and left in upright position for 15 minutes. Then they were measured in an automated gamma-counter (LKB-Wallac Ultro Gamma II). The resulting standard curve for this embodiment is shown in FIG. 2.

I claim:

1. A composition for separating free and bound radioligands within a radioimmunoassay, said bound radioligand being formed as a reaction product from reagents of the radioimmunoassay; the composition comprising individual particles capable of sedimenting in said assay and containing:
   (1) as a first active component, an attenuator having a high capacity to absorb emitted radiation of the radioligand and being selected from the group consisting of silver, cadmium, tungsten, bismuth and oxides thereof, and
   (2) as a second active component a material capable of binding said free radioligand or reaction product and being selected from the group consisting of charcoal, antibodies, antigens and biologically non-immune active binders.

2. The composition of claim 1 wherein said first active component is dispersed within a support matrix and said second active component is covalently coupled to the surface of said support matrix.

3. The composition of claim 2 wherein said first active component is bismuth oxide, said second active component is a first antibody and said support matrix is polyacrylamide.

4. The composition of claim 2 wherein said first active component is bismuth oxide, said second active component is a second antibody and said support matrix is polyacrylamide.

5. The composition of claim 2 wherein said first active component is bismuth oxide, said second active component is an antigen and said support matrix is polyacrylamide.

6. The composition of claim 2 wherein said first active component is bismuth oxide, said second active component is a non-immune active binder and said support matrix is polyacrylamide.

7. The composition of claim 2, 3, 4, 5 or 6 wherein said second active component is covalently coupled to said support matrix through glutaraldehyde linking groups.

8. The composition of claim 1 in the form of particles having a size range of about 1 to 100 microns.

9. The composition of claim 1 wherein said first active component is bismuth oxide and said second active component is charcoal dispersed within a support matrix selected from the group consisting of agarose, starch, and polyvinylidenefluoride.

10. The composition of claim 9 wherein said composition is in the form of particles having a size range of about 1 to 100 microns.

11. A composition comprising individual particles each containing bismuth oxide as a first active component dispersed within a polyacrylamide support matrix, and a non-immune type binder as a second active component covalently coupled to the surface of said support matrix.

* * * * *